US012263236B1

(12) United States Patent
Silver

(10) Patent No.: US 12,263,236 B1
(45) Date of Patent: *Apr. 1, 2025

(54) SODIUM LAUROYL SARCOSINATE CONTAINING DETERGENT COMPOSITIONS

(71) Applicant: WILLIAM M. YARBROUGH FOUNDATION, Peoria, IL (US)

(72) Inventor: Michael Edward Silver, Lake City, MI (US)

(73) Assignee: The William Yarbrough Foundation, Peoria, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/628,696

(22) Filed: Apr. 6, 2024

Related U.S. Application Data

(63) Continuation of application No. 17/543,009, filed on Dec. 6, 2021, now Pat. No. 11,951,200, which is a continuation of application No. 16/825,790, filed on Mar. 20, 2020, now Pat. No. 11,191,708.

(60) Provisional application No. 62/977,590, filed on Feb. 17, 2020.

(51) Int. Cl.
| | | |
|---|---|---|
| A61K 8/42 | (2006.01) | |
| A61K 8/02 | (2006.01) | |
| A61K 8/19 | (2006.01) | |
| A61K 8/34 | (2006.01) | |
| A61K 8/41 | (2006.01) | |
| A61K 8/44 | (2006.01) | |
| A61K 8/49 | (2006.01) | |
| A61K 8/81 | (2006.01) | |
| A61K 8/89 | (2006.01) | |
| A61Q 19/10 | (2006.01) | |
| C11D 1/04 | (2006.01) | |
| C11D 1/72 | (2006.01) | |
| C11D 3/12 | (2006.01) | |
| C11D 3/22 | (2006.01) | |
| C11D 3/37 | (2006.01) | |
| C11D 17/00 | (2006.01) | |

(52) U.S. Cl.
CPC ............. *A61K 8/42* (2013.01); *A61K 8/0216* (2013.01); *A61K 8/19* (2013.01); *A61K 8/342* (2013.01); *A61K 8/416* (2013.01); *A61K 8/44* (2013.01); *A61K 8/4973* (2013.01); *A61K 8/8147* (2013.01); *A61K 8/89* (2013.01); *A61Q 19/10* (2013.01); *C11D 1/04* (2013.01); *C11D 1/72* (2013.01); *C11D 3/1213* (2013.01); *C11D 3/221* (2013.01); *C11D 3/3738* (2013.01); *C11D 3/3761* (2013.01); *C11D 17/0039* (2013.01); *C11D 2111/12* (2024.01)

(58) Field of Classification Search
CPC .......... A61K 8/42; A61K 8/0216; A61K 8/19; A61K 8/342; A61K 8/44; C11D 1/72; C11D 3/1213; C11D 3/221; C11D 3/3738; C11D 3/3761
See application file for complete search history.

(56) References Cited

U.S. PATENT DOCUMENTS

| | | | |
|---|---|---|---|
| 6,423,746 B1 * | 7/2002 | Yarbrough | A61K 31/05 514/561 |
| 7,008,963 B2 | 3/2006 | Yarbrough | |
| 7,858,570 B2 * | 12/2010 | Hare | A61P 17/00 510/130 |
| 8,067,358 B1 | 11/2011 | Smith et al. | |
| 11,154,486 B2 * | 10/2021 | Silver | A61K 8/342 |
| 11,191,708 B2 * | 12/2021 | Silver | A61K 8/8147 |
| 11,857,666 B2 * | 1/2024 | Silver | A61K 8/44 |
| 11,951,200 B2 * | 4/2024 | Silver | A61K 8/4973 |
| 2002/0183284 A1 * | 12/2002 | Yarbrough | A61K 31/195 424/94.4 |
| 2006/0147405 A1 | 7/2006 | Yarbrough | |
| 2006/0147484 A1 * | 7/2006 | Hestand | A61K 33/14 424/401 |
| 2006/0177400 A1 * | 8/2006 | Yarbrough | A61K 9/0014 514/63 |
| 2006/0177406 A1 * | 8/2006 | Niazi | A61Q 19/10 424/70.22 |
| 2006/0275333 A1 * | 12/2006 | Trimble | A61Q 17/00 424/401 |
| 2007/0059268 A1 * | 3/2007 | Magee | A61K 8/44 424/70.21 |
| 2008/0107742 A1 * | 5/2008 | Hare | A61K 31/125 424/489 |
| 2008/0194662 A1 | 8/2008 | Kunin | |
| 2009/0191248 A1 * | 7/2009 | Hoffman | A61K 8/43 510/138 |

(Continued)

FOREIGN PATENT DOCUMENTS

| | | | |
|---|---|---|---|
| ES | 2688360 T3 | 11/2018 | |
| WO | WO-0202104 A1 * | 1/2002 | ............. A61K 31/03 |
| WO | WO-2015171986 A1 * | 11/2015 | ........... A61K 8/0241 |

OTHER PUBLICATIONS

United States Patent and Trademark Office, Non-Final Office Action issued in connection with U.S. Appl. No. 16/825,790, dated Nov. 4, 2020, 21 pages.

(Continued)

*Primary Examiner* — Peter F Godenschwager
*Assistant Examiner* — M. Reza Asdjodi
(74) *Attorney, Agent, or Firm* — Nyemaster Goode P.C.

(57) ABSTRACT

A detergent composition and a method of washing/cleaning urushiol at least partially, more typically substantially or completely off a surface of human skin or clothing. The detergent composition is typically a non-buffered composition that contains one or more $C_{12}$ surfactants, typically at least a sodium lauroyl sarcosinate and the detergent composition is typically free of one or more of (1) any nonylphenol ethoxylate; (2) any pharmaceutically active drug or prodrug; (3) any salt in an amount that affects the functional characteristics of either of the solely $C_{12}$ surfactants; (4) any salt in granular form; and/or (5) any ethoxylate that is a stand-alone ingredient.

19 Claims, No Drawings

(56) References Cited

U.S. PATENT DOCUMENTS

| | | | |
|---|---|---|---|
| 2014/0377337 A1* | 12/2014 | Steigerwalt, Jr. | A61K 9/12 |
| | | | 514/573 |
| 2015/0057255 A1* | 2/2015 | Zhang | A61K 9/2009 |
| | | | 514/416 |
| 2016/0338973 A1* | 11/2016 | Sonti | A61P 31/10 |
| 2016/0376263 A1* | 12/2016 | Patron | A61K 8/4973 |
| | | | 514/784 |
| 2017/0087199 A1* | 3/2017 | Patron | A61K 31/381 |
| 2019/0216779 A1 | 7/2019 | Basta et al. | |
| 2022/0087915 A1* | 3/2022 | Silver | A61K 8/19 |

OTHER PUBLICATIONS

United States Patent and Trademark Office, Non-Final Office Action issued in connection with U.S. Appl. No. 16/795,247, dated May 11, 2020, 13 pages.

Pankaj Karande et al., Synergistic effects of chemical enhancers on skin permeability: A case of sodium auroylsarcosinate and sorbitan monolaurate, European Journal of Pharmaceutical Scienes 31 (2007), pp. 1-7.

Rhein et al., "Interfacial Phenomena in Biological Systems", Surfactant Science Series, 1991, pp. 46-48, vol. 39.

* cited by examiner

SODIUM LAUROYL SARCOSINATE CONTAINING DETERGENT COMPOSITIONS

CROSS-REFERENCE TO RELATED APPLICATIONS

This application is a continuation of U.S. application Ser. No. 17/543,009, filed on Dec. 6, 2021, entitled "SODIUM LAUROYL SARCOSINATE CONTAINING DETERGENT COMPOSITIONS", which claims priority and benefit to U.S. application Ser. No. 16/825,790, filed on Mar. 20, 2020, entitled "SODIUM LAUROYL SARCOSINATE CONTAINING DETERGENT COMPOSITIONS", now U.S. Pat. No. 11,191,708, which claims priority to and the benefit of U.S. Application Ser. No. 62/977,590, filed on Feb. 17, 2020, entitled "Sodium Lauroyl Sarcosinate Containing Detergent Compositions," the disclosures of which are hereby incorporated by reference in their entirety.

BACKGROUND

Urushiol-induced contact dermatitis (also called *Toxicodendron* dermatitis and *Rhus dermatitis*) is produced by the oil urushiol. Urushiol is contained in various plants, including the plants of the family Anacardiaceae, especially the species *Toxicodendron*, which includes poison ivy, poison oak, and poison sumac. Other plants in the family Anacardiaceae, such as mango, Rengas tree, Burmese lacquer tree, India marking nut tree, and the shell of the cashew nut. A few unrelated plants, such as *Ginkgo biloba*, also contain urushiol. Poison ivy, poison oak, and poison sumac grow in wooded or marshy areas throughout North America. The plants aren't really poisonous. The urushiol causes an itchy, blistering rash after it touches a human's skin. Even slight contact, like brushing up against the leaves, can leave the oil behind. Poison sumac is a shrub or tree. Poison ivy and poison oak grow as vines or shrubs.

Symptoms of urushiol-induced contact dermatitis include itching, inflammation, oozing, and in severe cases, a burning sensation. Urushiol-induced contact dermatitis is contracted by contact with a plant or any other object containing urushiol oil. The oil adheres to almost anything with which it comes in contact, such as skin; essentially any fabric product such as towels, blankets, and clothing; and gear such as backpacks. Any surface contacting the plant and then contact with the skin typically causes exposure to the oil. Normally, it takes about 24 hours for the rash to first appear. Oftentimes, the rash will worsen over a period of a few days. When someone has a severe reaction to urushiol, a prednisone prescription is necessary to stop skin damage, especially if the eyes or other sensitive part of the human anatomy has been exposed to the oil or exhibits an allergic reaction to the oil. The urushiol induced dermatitis rash often persists typically for one to two weeks but in some cases can last as long as five weeks. Since the skin reaction is an allergic one, some people may mount progressively stronger reactions after repeated exposures. People vary greatly in their sensitivity to urushiol. In up to 30% of people, urushiol does not trigger an immune response; however, if it does, the rash and effects are irritating and can be very serious.

Urushiol is an oily mixture of organic compounds. It is a yellow liquid. It is soluble in ethanol, diethyl ether, and benzene. Urushiol is a mixture of several closely related organic compounds. Each consists of a catechol substituted in the 3 position with a hydrocarbon chain that has 15 or 17 carbon atoms. The hydrocarbon group may be saturated or unsaturated. The exact composition of the mixture varies, depending on the plant source. Whereas western poison oak urushiol contains chiefly catechols with C17 side-chains, poison ivy and poison sumac contain mostly catechols with C15 sidechains. Typically, Urushiol has the chemical structure below:

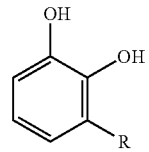

where R is one of the following: $(CH_2)_{14}CH_3$; $(CH_2)_7 CH=CH(CH_2)_5CH_3$; $(CH_2)_7CH=CHCH_2CH=CH(CH_2)_2 CH_3$; $(CH_2)_7CH=CHCH_2CH=CHCH=CHCH_3$; or $(CH_2)_7 CH=CHCH_2CH=CHCH_2CH=CH_2$.

There are various compositions that have been developed or proposed for use in connection with the treatment of these symptoms/effects. Typically, treatment for urushiol induced contact dermatitis includes first stopping contact with the urushiol source or oil containing surface and later reducing the pain and/or itching. The primary treatment employed is typically washing of the skin with detergent, cool water and friction as soon as possible after the discovery that the skin has been exposed to urushiol.

There are various previously used treatments of urushiol-induced contact dermatitis including washing compositions or compositions that medicinally temporarily reduce the itching and perhaps some of the other symptoms caused by contact with urushiol. Most such compositions use a nonylphenol ethoxylate, in particular, nonoxynol 9. Nonylphenol ethoxylate exist and are sold and employed in pharmaceutical compositions typically as a stand-alone end product/ingredient and not generally mixed with other compounds to form a final product that is typically used/incorporated into an end product containing multiple compound/ingredient containing overall compositions. Nonoxynol 9 is a surfactant spermicide primarily used for contraception in spermicidal creams, jellies, foams, gel, and lubricants. It is also used in conjunction with other methods of contraception, including condoms, cervical caps and diaphragms. It is also used in certain detergents and other products. However, there are very significant environmental problems associated with the use of nonylphenol ethoxylate in any detergent/cleansing composition that will be washed into an aquatic environment or into a septic or water treatment system. In particular, the Environmental Protection Agency (EPA) in the U.S. has noted that nonylphenol (NP) is persistent in the aquatic environment, moderately bioaccumulative, and extremely toxic to aquatic organisms. Furthermore, NP has also been shown to exhibit estrogenic properties in in vitro and in vivo assays. NP's main use is in the manufacture of nonylphenol ethoxylates (NPEs). Under the Toxic Substances Control Act (TSCA), in 2014, the EPA proposed a significant new use rule (SNUR) to require Agency review before a manufacturer begins or resumes use of 15 NPs and NPEs.

The use of NPEs in household laundry detergents is thought to have been completely phased out (U.S. EPA 2010b). Proctor and Gamble, the leading household liquid laundry detergent vendor in the U.S. (Statista 2017), stopped using them around 2005 (Proctor & Gamble 2005) and Walmart and Target added them to their priority list of chemicals for their suppliers to remove from products in 2015 and 2016, respectively. The use of laundry detergents containing NPEs by industrial laundries has also declined. In 2010, the Textile Retail Services Association (TRSA), representing approximately 98 percent of industrial laundry facilities in the United States, entered into a voluntary agreement with EPA to phase out the use of NPEs in detergents by 2014 (TRSA 2010). While significant progress has been made towards implementing this agreement, U.S. EPA estimates it only covers approximately 50 percent of NPE laundry detergent use, and the complete phase-out has not been confirmed. In fact, nonoxynol-9 carries with it a GHS Hazard Statement H411 that it is toxic to aquatic life with long lasting effects.

SUMMARY

An aspect of the present disclosure is generally directed toward a method of at least partially cleaning a surface comprising the steps of: washing an area of a person's skin having urushiol thereon or an item of clothing having urushiol on a surface thereof with a detergent composition; and rinsing the detergent composition from the area. The detergent composition includes a sodium lauroyl sarcosinate, is typically not buffered; and is typically free of at least one and typically all of the following: (1) any nonylphenol ethoxylate, (2) any pharmaceutically active drug or prodrug, (3) any salt in granular form; and (4) any ethoxylate that is a stand-alone ingredient.

Another aspect of the present disclosure is generally directed to a method of washing urushiol from the surface of human skin that includes the steps of: applying a detergent composition to at least an area of a human's skin exposed to urushiol; washing the area; and rinsing the composition from the area. The detergent composition typically consists essentially of: water; a hydrophilic, and cross-linked polyacrylic acid polymer; at least one type of bio-degradable bead having a maximum particle size of 300 microns; a silicone copolyol wetting agent; a first $C_{12}$ surfactant that comprises a sodium lauroyl sarcosinate; optionally, a second $C_{12}$ surfactant is a non-ionic $C_{12}$ surfactant; a non-ionic polyethylene glycol ether of a mixture of synthetic $C_{12-15}$ fatty alcohols with an average of 9 moles of ethylene oxide; a quaternary ammonium salt; a disodium EDTA; and a sodium hydroxide.

Another aspect of the present disclosure is generally directed toward a method of washing urushiol off the surface of human skin that includes the steps of: applying a cleaning composition to at least an area of a human's skin exposed to urushiol; washing the area; and rinsing the cleaning composition from the area and the rinsed cleaning composition does not affect marine life reproduction. The cleaning composition typically consists of: water; a hydrophilic, and cross-linked polyacrylic acid polymer; at least one type of bio-degradable bead having a maximum particle size of 300 microns; a silicone copolyol wetting agent; a sodium lauroyl sarcosinate solution; optionally a second $C_{12}$ surfactant; a non-ionic polyethylene glycol ether of a mixture of synthetic $C_{12-15}$ fatty alcohols with an average of 9 moles of ethylene oxide; a quaternary ammonium salt; a disodium EDTA; and a sodium hydroxide.

These and other aspects, objects, and features of the present invention will be understood and appreciated by those skilled in the art upon studying the following specification, claims, and appended drawings.

DETAILED DESCRIPTION

It is to be understood that the invention may assume various alternative orientations, except where expressly specified to the contrary. It is also to be understood that the specific devices and processes illustrated in the attached drawings, and described in the following specification are simply exemplary embodiments of the inventive concepts defined in the appended claims. Hence, specific dimensions and other physical characteristics relating to the embodiments disclosed herein are not to be considered as limiting, unless the claims expressly state otherwise. All ranges and parameters, including but not limited to percentages, parts, and ratios, disclosed herein are understood to encompass any and all sub-ranges assumed and subsumed therein, and every number between the endpoints. For example, a stated range of "1 to 10" should be considered to include any and all sub-ranges beginning with a minimum value of 1 or more and ending with a maximum value of 10 or less (e.g., 1 to 6.1, or 2.3 to 9.4), and to each integer (1, 2, 3, 4, 5, 6, 7, 8, 9, 10) contained within the range. In this specification and the appended claims, the singular forms "a," "an" and "the" include plural reference unless the context clearly dictates otherwise. All combinations of method steps or process steps as used herein can be performed in any order, unless otherwise specified or clearly implied to the contrary by the context in which the referenced combination is made.

The various embodiments of the urushiol treating detergent/detergent compositions of the present disclosure may also be substantially free of any ingredient or feature described herein, provided that the remaining composition still contains all of the required ingredients or features as described herein. In this context, and unless otherwise specified, the term "substantially free" means that the selected composition contains less than a functional amount of the optional ingredient, typically less than 1%, including less than 0.5%, including less than 0.1%, and also including zero percent, by weight of such optional or selected essential ingredient.

The compositions of the present disclosure described herein, including but not limited to, the detergent compositions for washing urushiol off of skin, detergent compositions for treating urushiol induced contact dermatitis and methods of treating urushiol on the skin and removing it using the detergent compositions described herein as well as methods of treating urushiol induced contact dermatitis, and corresponding manufacturing methods may comprise, consist of, or consist essentially of the elements of the products as described herein, as well as any additional or optional element described herein or otherwise useful in topical wash product applications. Typically, the detergent compositions of the present disclosure are free of pharmaceutically active ingredients/drug(s), sodium chloride (NaCl)/any granulated salt (NaCl), and nonylphenol ethoxylate(s) such as Nonoxyl-9. The detergent compositions of the present disclosure are also typically free of any ethoxylate that is a stand-alone ingredient. "Consisting essentially of" in the context of the claims of this application limits the scope of a claim or claim element to the specified materials or steps "and those that do not materially affect the basic and novel characteristic(s)" of the claimed invention as would be known by those of ordinary skill in the art whether or not such a composition is disclosed in the application or not as affecting the basic and novel characteristic. For example, in the case of granular salt (NaCl), this ingredient, if added to detergent compositions of the present disclosure containing sodium lauroyl sarcosinate (SLS), materially affects the surface tension and other performance characteristics of the SLS and any other surfactant that may be present in the detergent compositions of the present disclosure.

To the extent that the term "includes" or "including" is used in the specification or the claims, it is intended to be inclusive in a manner similar to the term "comprising" as that term is interpreted when employed as a transitional word in a claim. Furthermore, to the extent that the term "or" is employed (e.g., A or B) it is intended to mean "A or B or both." When the Applicant intends to indicate "only A or B but not both" then the term "only A or B but not both" will be employed. Thus, use of the term "or" herein is the inclusive, and not the exclusive use. Also, to the extent that the terms "in" or "into" are used in the specification or the claims, it is intended to additionally mean "on" or "onto."

The term "ingredient" as used herein refers to a component of a detergent composition of the present disclosure that is a non-custom (i.e. not specifically blended, but generally available) ingredient purchased from a supplier prior to being mixed or combined with another component of the overall detergent composition of the present disclosure. Relatedly, a "stand-alone ingredient" as used herein refers to an ingredient of the detergent composition(s) of the present disclosure as purchased from a supplier that is used to make an overall detergent composition in the context of the present disclosure where the ingredient is the ingredient mentioned or the ingredient mentioned in a solvent such as water and not a mixture of active components; however, a stand-alone ingredient does include an aqueous composition including a single active or another solution containing a single active ingredient (the solute) in a solvent. Relatedly, a "blended ingredient" as used herein refers to an ingredient of the detergent composition(s) of the present disclosure purchased from a supplier that is used to make an overall detergent composition in the context of the present disclosure where the blended ingredient includes more than a single active component other than a solvent when purchased from the supplier. Stand-alone ingredients and blended ingredients may be combined together to create compositions of the present disclosure.

Main Components of the Detergent Compositions of the Present Disclosure

The overall composition of the present disclosure typically includes water, more typically deionized water. Water can be included in an amount of from about 40-60 weight percent of the overall compositions. Water is a part of some of the raw material components of the composition and added as a separate additive. The typical formulas of the present disclosure have water added independently in an amount of about 40-60 weight percent water as a separate and independent component. Water is also typically contributed by two other components of the compositions of the present disclosure.

Unlike many detergent compositions used to wash urushiol from a surface of clothing or skin, the compositions of the present disclosure typically contain sodium lauroyl sarcosinate (SLS) as the primary or sole ingredient with efficacy to remove urushiol from clothing and/or skin. Sodium lauroyl sarcosinate is a stand-alone ingredient when used in the context of the present disclosure. Sodium lauroyl sarcosinate (SLS) alone is effective to remove urushiol from skin, especially when used with scrubbing beads. The sodium lauroyl sarcosinate is typically used as one ingredient in a non-buffered detergent composition according to the present disclosure and the detergent compositions of the present disclosure are typically free of at least one or more of the following that have a deleterious effect on the detergent composition and/or the environment: (1) any nonylphenol ethoxylate, in particular any ethoxylate that breakdown to a nonylphenol when exposed to the ambient environment, (2) any pharmaceutically active drug or prodrug, (3) any salt, including granular sodium chloride, that affects the functional characteristics of the sodium lauroyl sarcosinate (SLS), (4) a salt in granular form; and/or (5) any ethoxylate not a part of another surfactant component that may optionally be included. The sodium lauroyl sarcosinate (SLS) is typically the only surfactant ingredient, either stand-alone ingredient or blended ingredient added to and effective for removing urushiol from the surface of clothing or skin, other surfactants may be included in the detergent compositions, if desired, and are typically selected if included to remove dirt and other oils from the clothing or skin cleaned by the detergent compositions of the present disclosure. Sodium lauroyl sarcosinate is an anionic surfactant and foaming agent and is derived from sarcosine. It is a sodium salt of lauroyl sarcosine. It generally conforms to the formula:

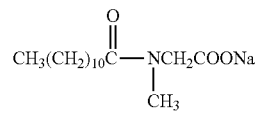

The percentage of sodium lauroyl sarcosinate is generally present in the detergent composition in an amount up to about 1.5% by weight of the detergent composition; however, the sodium lauroyl sarcosinate may be present in the detergent composition in an amount of up to about 10%, about 15%, about 20% or even 50% or about 50% by weight of the overall detergent composition. It is typically a white solid in pure form and produces a colorless to light yellow aqueous solution.

Sorbitan monolaurate can also be added as another $C_{12}$ surfactant ingredient, typically as a stand-alone ingredient, in the detergent compositions of the present disclosure. SPAN® 20, a sorbitan monolaurate, is a sorbitan ester and significantly is also a biodegradable surfactant based on a natural fatty acid (lauric acid) and sugar alcohol sorbitol. This sorbitan ester is highly effective at forming oil in water emulsions. Sorbitan monolaurate is a non-ionic surfactant that is a mixture of esters formed from the fatty acid lauric acid and polyols derived from sorbitol, including sorbitan and isosorbide and has a chemical structure of $C_{18}H_{34}O_6$. A derivative of sorbitan monolaurate such as its ethoxylated derivative, TWEEN® 20 may be used in place of some or all of the sorbitan monolaurate if it is used in the detergent compositions of the present disclosure. When used, the sorbitan monolaurate is typically present in an amount of from about 0.5 percent to as much as about 50 percent by weight of the overall detergent composition, more typically in an amount of about 2.0% or 10% by weight of the overall detergent composition. The sodium lauroyl sarcosinate is typically added in the form of an aqueous solution with 30% of the solution being sodium lauroyl sarcosinate, but no other surfactant component is typically present in the aqueous solution when it is supplied from the supplier or prior to when it is added to one or more of the other components of the detergent compositions of the present disclosure. Sodium lauroyl sarcosinate is typically present in slightly lower amounts than the amount of the sorbitan monolaurate. When sorbitan monolaurate is present in the detergent compositions of the present disclosure, the sodium lauroyl sarcosinate and sorbitan monolaurate are present in a ratio based on the percent of active ingredient in the overall composition in a ratio range of from 1 part sodium lauroyl sarcosinate to up to 2.5 parts sorbitan monolaurate. While a lower amount of sodium lauroyl sarcosinate than sorbitan monolaurate is typically used, amounts of sodium lauroyl sarcosinate may be used in higher amounts as well, as discussed above, including up to 10%, 15%, 20% or even 50% by weight of the overall detergent composition. The amount of sodium lauroyl sarcosinate is typically from about 1.0% to about 10% by weight of the overall detergent composition when used to remove urushiol from skin. The amount of sodium lauroyl sarcosinate is typically present about the same amounts by weight of the overall detergent composition when the detergent composition is to be used to remove urushiol from clothing. When higher amounts are included less water is added as a separate and independent component at least until the skin or clothing are cleaned/washed when excess water is added to wash the affected areas of skin or clothing.

The detergent compositions of the present disclosure may include a quaternary ammonium salt such as quaternium-15. It acts as an antimicrobial agent/preservative because it acts as a formaldehyde releaser. Any known preservative may be used instead of or in addition to the quaternary ammonium salt, quaternium-15.

Another component that is typically present in the detergent compositions of the present disclosure is $C_{12-15}$ Pareth-9. $C_{12-15}$ Pareth-9, which contains a mixture of C12, C13, C14 and C15 components, is a surfactant that may be used in the compositions of the present disclosure. The $C_{12-15}$ Pareth-9 is a blended ingredient. $C_{12-15}$ Pareth-9 is a polyethylene glycol ether of a mixture of synthetic $C_{12-15}$ fatty alcohols with an average of 9 moles of ethylene oxide. It is a non-ionic surfactant. $C_{12-15}$ Pareth-9 is a blended ingredient when purchased from a supplier. $C_{12-15}$ Pareth-9 is a lightweight, synthetic mixture of fatty alcohols and polyethylene glycols that functions as an emulsifier and surfactant, in particular a non-ionic surfactant.

The detergent compositions of the present disclosure also typically contain a CARBOPOL", which is a high molecular weight, hydrophilic, and cross-linked polyacrylic acid polymer. This physical hydrogel presents a three-dimensional polymer network that is swollen by water, and presents temporary, reversible inter-chain entanglements that are stronger when compared to chemical hydrogels. The particularly preferred CARBOPOL® of the present disclosure is CARBOPOL® 980 polymer, which is a white powder, cross-linked polyacrylic acid that is polymerized in a toxicologically-preferred co-solvent system. It is an extremely efficient rheology modifier capable of providing high viscosity and forms sparkling clear gels or hydro-alcoholic gels and creams. CARBOPOL® 980 has a viscosity of 40,000-60,000 cP (0.5% at pH 7.5) and a monomer molecular weight of 72.02 g/mol.

The overall detergent compositions of the present disclosure typically have a pH of from about 5.5 to 7.0, is typically un-fragranced, white to off-white and an opaque creamy lotion when used to cleanse skin and can be a liquid form if further diluted with additional water when used to clean clothing having urushiol. When scrubbing beads are employed in the composition for cleaning the skin of urushiol the scrubbing breads make the composition have a gritty texture.

When one or more kinds of scrubbing beads are employed in connection with the detergent compositions of the present disclosure, the beads are typically beads that are bio-degradable beads. However, polyethylene beads may also be employed as well. Sasol Ltd. DECORNEL® 300 synthetic wax polymer beads or Micro Powders Inc. SYNSCRUB® 50PC high molecular weight synthetic wax polymer beads or Low Density Polyethylene (LDPE) beads may be used. The synthetic wax used in DECORNEL® and SYNSCRUB® products is biodegradable. As such, this material is preferred over polyethylene beads, which have a very long degradation timetable comparatively-especially since the detergent compositions of the present disclosure are skin washing compositions where the material is washed into the water treatment system/plumbing systems and may ultimately reach a natural body of water. The use of biodegradable beads in some form allows the detergent compositions of the present disclosure to completely biodegrade in ambient environment after 2 years. Additionally, the at least one type of bio-degradable beads of the present disclosure biodegrades in an ambient environment by 33.8% after 86 days according to the Organization for Economic Co-operation and Development Test Guideline 302 C entitled Inherent Biodegradability: Modified MITI Test (II).

DECORNEL® 300 by Sasol acts as a consistency regulator, exfoliating and cleansing agent. It is a nonpolar, white, tasteless and odorless wax bead. It is a blend consisting predominantly of saturated n-alkanes, highly refined. It is available in 50-300 μm particle size. It is 100% hydrophobic and preservative-free. It is non-ionic and has no impact on the pH value of the overall composition when incorporated into compositions of the present disclosure. It offers consistent high quality and removes dead cells smoothly. It can outperform polyethylene beads in face, hand and foot scrubs as well as toothpaste. DECORNEL® 300 is synthesized from carbon monoxide and hydrogen in accordance with the Fischer-Tropsch method. It can replace plant waxes, hydrogenated fats and other hard base substances in products. As stated above, it does not influence the pH-value and can be applied in formulas with a pH-value of 3-11. It is a very pure product and inherent primary biodegradable in the terms of the OECD Test 301-B/302-C. DECORNEL® 300 has a shelf life of 60 months.

SYNSCRUB® 50PC is a synthetic wax powder. It is designed for use as an economical exfoliating agent and has an irregular particle shape which produces the same high performance as commonly used irregular particle shape polyethylene powders. It is, however, biodegradable. SYNSCRUB® 50PC has a maximum mesh side of 50 and a maximum particle size of 297 microns. Its density at 77° F. is 0.95.

Another component of the typical detergent composition is a PEG-12 dimethicone, which belongs to the class of dimethyl-methyl(polyethyleneoxide) siloxanes. It is presently believed that any dimethyl-methyl(polyethyleneoxide) siloxane may be used or a plurality of dimethyl-methyl (polyethyleneoxide) siloxanes may be used in the detergent compositions of the present disclosure. When used, the PEG-12 dimethicone (or one or more dimethyl-methyl(polyethyleneoxide) siloxanes) is typically present in an amount of from about 0.8% by weight to about 1.2% by weight of the overall detergent composition. It acts as a surface tension depressant, wetting agent, emulsifier and foam builder. PEG-12 dimethicone gives a stable foam. The PEG-12 dimethicone is a silicone copolyol wetting agent. If a wetting agent is used, it must be soluble in water and not dispersible or insoluble, which could result in deposits that clog or block hair follicles into which urushiol has migrated or harm clothing being treated with the detergent composition. The wetting agent's hydrophilic-lipophilic balance is typically 10 or higher on the HLB scale from 0 to 20.

The detergent compositions of the present disclosure also typically include disodium EDTA. Disodium EDTA is also known as Disodium ethylenediaminetetraacetic acid. Disodium EDTA is used as a chelating agent that sequesters a variety of polyvalent cations such as calcium. Chelating agents are chemical compounds that react with metal ions to form a stable, water-soluble complex. Chelating agents have a ring-like center which forms at least two bonds with the metal ion allowing it to be excreted. Disodium EDTA has a molecular weight of 338.22 g/mol and is a white crystalline powder. Disodium EDTA is typically included in the compositions of the present disclosure in an amount of from about 0.8% to 1.2% by weight of the overall composition.

Finally, the detergent compositions of the present disclosure typically also include an amount of sodium hydroxide (25%). The sodium hydroxide is typically present in an amount of the overall composition to neutralize CARBOMER® and achieve a desirable pH.

Additional Optional Ingredients

It will be understood by one having ordinary skill in the art that construction of the described invention and other components is not limited to any specific material. Other exemplary embodiments disclosed herein may be formed from a wide variety of materials, unless described otherwise herein. The detergent compositions and methods of treatment of the present disclosure may further comprise optional components that may modify the physical, chemical, aesthetic or processing characteristics of the formulas or serve as pharmaceutical or additional components when used in a targeted population. Non-limiting examples of such optional ingredients include preservatives, anti-oxidants, emulsifying agents, colorants, and related derivatives, thickening agents and stabilizers, and other additive or synergistic ingredients that will be appreciated in the art of urushiol treating composition formulation. However, the detergent compositions of the present disclosure, as discussed above, will typically not include and are free of any nonylphenol ethoxylate, more typically any ethoxylate containing one or more benzene ring or cyclic component, even more typically any ethoxylate that is not part of the non-ionic polyethylene glycol ether of a mixture of synthetic $C_{12-C15}$ fatty alcohols with an average of 9 moles of ethylene oxide; granulated salt; or pharmaceutically active component used to treat urushiol including, but not limited to, neurokinin-1 (NK-1) antagonists, such as serlopiltant. Additionally, the compositions of the present disclosure typically also do not utilize the surfactants in any type of buffered solution and the overall detergent compositions are not buffered either.

It is also to be understood that variations and modifications can be made on the aforementioned compositions and methods without departing from the concepts of the present invention, and further it is to be understood that such concepts are intended to be covered by the following claims unless these claims by their language expressly state otherwise.

When forming the compositions of the present disclosure, a container is charged with the deionized water first, thereafter, the CARBOMER® is added using a lightning mixer or tri-blender. Once the CARBOMER® is completely hydrated the remaining ingredients are usually added in the order listed above. Each ingredient is mixed well between each addition. Typically, sodium hydroxide is the final ingredient added.

Use and Application of Detergent Compositions to Clean Urushiol

In use, the detergent compositions of the present disclosure may be used to clean urushiol from skin and treat urushiol induced contact dermatitis. The detergent compositions may also be used to clean clothing that has come into contact with urushiol. When a detergent composition of the present disclosure is used to clean the skin, the detergent composition is typically applied directly or indirectly to the skin exposed to urushiol after the composition is hydrated, typically by wetting the detergent composition in the user's hands for about 10 seconds until the product is worked into a paste form. The paste should then be rubbed on the affected area of the skin for up to 3 minutes until there is no sign of itching (about 15 seconds is typical for mild to moderate reactions to urushiol). Thereafter, the area should be rinsed thoroughly. If itching returns, the process may be repeated any number of times. Typically, only a few treatments will be necessary. The methods of treating contact dermatitis and the methods of washing skin exposed to urushiol of the present disclosure typically include the above steps.

What is claimed is:

1. An unbuffered detergent composition that is environmentally friendly for cleaning a surface of urushiol, wherein the unbuffered detergent composition comprises:
    water in an amount of from 40 to 60 weight percent of the unbuffered detergent composition; surfactants, wherein the surfactants consist of a sodium lauroyl sarcosinate, a sorbitan monolaurate, and a non-ionic polyethylene glycol ether of a mixture of synthetic C12-15 fatty alcohols with an average of 9 moles of ethylene oxide;
    at least one type of bio-degradable bead having a maximum particle size of 300 microns;
    wherein the unbuffered detergent composition is free of any ethoxylate that is not part of the nonionic polyethylene glycol ether of a mixture of synthetic C12-C15 fatty alcohols with an average of 9 moles of ethylene oxide;
    wherein the unbuffered detergent composition is free of any of the following: (1) any nonylphenol ethoxylate, (2) any pharmaceutically active drug or prodrug, (3) any salt in granular form; and (4) any ethoxylate that is a stand-alone ingredient; and
    wherein the unbuffered detergent composition completely biodegrades in an ambient environment after 2 years.

2. The unbuffered detergent composition of claim 1, wherein the at least one type of bio-degradable bead degrades by around 33.6 percent in an ambient environment after 86 days.

3. The unbuffered detergent composition of claim 1, wherein the sodium lauroyl sarcosinate is in an amount of about 1.5 percent to about 50 percent by weight of the unbuffered detergent composition.

4. The unbuffered detergent composition of claim 1, wherein the sorbitan monolaurate is in an amount of about 0.5 percent to about 50 percent by weight of the unbuffered detergent composition.

5. The unbuffered detergent composition of claim 4, wherein the sorbitan monolaurate is in an amount of from about 1.0 percent to about 10 percent by weight of the unbuffered detergent composition.

6. The unbuffered detergent composition of claim 1, wherein the water is added as a separate and independent component of the unbuffered detergent composition.

7. An unbuffered detergent composition for cleaning urushiol from a surface, wherein the unbuffered detergent composition comprises:
    water;
    a hydrophilic, and cross-linked polyacrylic acid polymer;
    at least one type of bio-degradable bead having a maximum particle size of 300 microns;
    a silicone copolyol wetting agent;
    a first solely C12 surfactant that is a non-ionic solely C12 surfactant;

a second solely C12 surfactant that is an anionic solely C12 surfactant;

a non-ionic polyethylene glycol ether of a mixture of synthetic C12-15 fatty alcohols with an average of 9 moles of ethylene oxide;

a quaternary ammonium salt;

a disodium EDTA;

a sodium hydroxide;

wherein the unbuffered detergent composition is free of each of the following: (1) any nonylphenol ethoxylate, (2) any pharmaceutically active drug or prodrug, (3) any salt in granular form; (4) any ethoxylate that is a stand-alone ingredient; and (5) any ethoxylate that is not part of the non-ionic polyethylene glycol ether of a mixture of synthetic C12-C15 fatty alcohols with an average of 9 moles of ethylene oxide; and wherein the unbuffered detergent composition completely biodegrades in an ambient environment after 2 years.

8. The unbuffered detergent composition of claim 7, wherein the water is in an amount of from 40 to 60 weight percent of the unbuffered detergent composition.

9. The unbuffered detergent composition of claim 7, wherein the first solely C12 surfactant is a sorbitan monolaurate.

10. The unbuffered detergent composition of claim 9, wherein the sorbitan monolaurate is in an amount of from about 0.5 percent to about 50 percent by weight of the unbuffered detergent composition.

11. The unbuffered detergent composition of claim 10, wherein the sorbitan monolaurate is in an amount of from about 1.0 percent to about 10 percent by weight of the unbuffered detergent composition.

12. The unbuffered detergent composition of claim 7, wherein the second solely C12 surfactant is sodium lauroyl sarcosinate.

13. The unbuffered detergent composition of claim 12, wherein the sodium lauroyl sarcosinate is in an amount of about 1.5 percent to about 50 percent by weight of the unbuffered detergent composition.

14. The unbuffered detergent composition of claim 7, wherein the at least one type of bio-degradable bead degrades by around 33.6 percent in an ambient environment after 86 days.

15. The unbuffered detergent composition of claim 7, wherein the pH of the unbuffered detergent composition is at range of about 5.5 to about 7.0.

16. The unbuffered detergent composition of claim 7, wherein the silicone copolyol wetting agent has a hydrophilic-lipophilic balance of 10 or higher and wherein the silicone copolyol wetting agent is soluble in water.

17. An unbuffered detergent composition for cleaning urushiol from a surface and that imparts fewer negative effects on the environment than other detergent compositions, wherein the unbuffered detergent composition comprises:

water;

a hydrophilic, and cross-linked polyacrylic acid polymer;

at least one type of bio-degradable bead having a maximum particle size of 300 microns;

a silicone copolyol wetting agent;

sodium lauroyl sarcosinate that is added as a stand-alone ingredient;

a non-ionic polyethylene glycol ether of a mixture of synthetic C12-15 fatty alcohols with an average of 9 moles of ethylene oxide;

a quaternary ammonium salt;

a disodium EDTA;

a sodium hydroxide;

wherein the unbuffered detergent composition is free of each of the following: (1) any nonylphenol ethoxylate, (2) any pharmaceutically active drug or prodrug, (3) any salt in granular form; (4) any ethoxylate that is a stand-alone ingredient; and (5) any ethoxylate that is not part of the non-ionic polyethylene glycol ether of a mixture of synthetic C12-C15 fatty alcohols with an average of 9 moles of ethylene oxide; and wherein the unbuffered detergent composition completely biodegrades in an ambient environment after 2 years.

18. The unbuffered detergent composition of claim 17 further comprising a C12 surfactant that is a non-ionic solely C12 surfactant and wherein the non-ionic solely C12 surfactant is sorbitan monolaurate.

19. The unbuffered detergent composition of claim 17, wherein the at least one type of bio-degradable bead degrades by around 33.6 percent in an ambient environment after 86 days.

* * * * *